United States Patent [19]
Weber et al.

[11] Patent Number: 6,114,348
[45] Date of Patent: Sep. 5, 2000

[54] METHOD OF TREATING WARTS USING TAZAROTENE

[76] Inventors: Paul J. Weber, 1 Seneca Rd., Ft. Lauderdale, Fla. 33308; Luiz B. Da Silva, 1995 Camino Ramon Pl., Danville, Calif. 94526; Michael R. Weber, 13906 Term La., Clearwater, Fla. 33762

[21] Appl. No.: 09/265,776

[22] Filed: Mar. 10, 1999

[51] Int. Cl.[7] .......................... A61K 31/44; A61K 31/56; A61K 31/505
[52] U.S. Cl. .......................... 514/299; 514/171; 514/181; 514/274
[58] Field of Search .................... 435/6; 514/171, 514/703, 381, 299, 274, 181; 424/195.1, 401

[56] References Cited

U.S. PATENT DOCUMENTS

| | | | |
|---|---|---|---|
| 4,877,805 | 10/1989 | Kligman | 514/381 |
| 5,492,935 | 2/1996 | Yu et al. | 514/703 |
| 5,643,584 | 7/1997 | Farng et al. | 424/401 |
| 5,776,687 | 7/1998 | Nagpal et al. | 435/6 |
| 5,855,893 | 1/1999 | Weinkauf et al. | 424/195.1 |
| 6,028,088 | 2/2000 | Pershadsingh et al. | 514/369 |

OTHER PUBLICATIONS

Weiss, Current options for the topical . . . , Pediatric Dermatology, vol. 14(6), p. 480–488, 1997.

*Primary Examiner*—William R. Jarvis
*Assistant Examiner*—Vickie Kim

[57] ABSTRACT

A method and composition for topically treating non-metastasizing skin eruptions of warts with tazarotene in a suitable pharmaceutical composition. The compositions can include corticosteroids or fluorouracil.

10 Claims, No Drawings

METHOD OF TREATING WARTS USING TAZAROTENE

FIELD OF THE INVENTION

The present invention relates to a method of treating certain non-metastasizing skin eruptions. More particularly, there is provided a method of treating warts and keratoacanthoma with a composition containing ethyl 6-[2-(4,4-dimethylthiochroman-6-yl)—ethynyl]nicotinate (Tazarotene) or the salts thereof.

BACKGROUND OF THE INVENTION

Warts are benign tumors that commonly involve skin and less frequently affect other epithelial tissues. These lesions are induced by papillomaviruses which are deoxyribonucleic acid (DNA)-containing viruses. The approach to treatment of warts depends on the age of the patient, the extent and duration of lesions and the patient's immunological status. Common therapy has been cryotherapy, using caustics and acids such as salicylic acid, lactic acid, trichloracetic acid or retinoic acid. Unfortunately, many warts resist such treatment, especially in organ transplant patients.

Keratoacanthoma is a common keratinizing cutaneous squamous neoplasm characterized by rapid and prolific growth sometimes followed by spontaneous involution, classically occurring on the sun-exposed skin of elderly light skinned individuals. There are several methods of treating keratoacanthomas. Surgical excision and injectable intralesional 5-fluorouracil have been used to remove lesions, but scarring occurs from surgery and necrosis of tissue occurs. 5-Fluorouracil has been used for solitary, multiple and large lesions. This treatment requires painful injections and needs to be complete to be effective. Corticosteroids have been used with variable success.

U.S. Pat. No. 5,089,509 to Chandraratna, which is herein incorporated by reference, discloses the preparation and use of tazarotene in the treatment of immunological disorders such as lupus, epithelial cancers and psoriasis.

SUMMARY OF THE INVENTION

The present invention relates to a method of treating non-metastasizing skin eruptions such as warts and keratoacanthomas with an effective amount of tazarotene in a pharmaceutical carrier.

Advantageously, the composition comprises a combination of tazarotene and fluorouracil.

It is additionally advantageous to utilize tazarotene in combination with a corticosteroid to treat keratoacanthomas.

It is therefore an object of the invention to treat warts and keratoacanthomas with a composition containing an effective amount of tazarotene or the salts thereof.

It is a further object of the invention to provide a method and composition comprising tazarotene or the salts thereof in combination with a corticosteroid to treat the lesions of keratoacanthomas and warts.

It is a further object of the invention to provide a composition for with treating warts and keratoacanthomas and other types of skin eruptions topically with a Tazarotene in combination with a corticosteroid or fluorouracil.

DESCRIPTION OF THE PREFERRED EMBODIMENTS

The present invention provides a method and compositions for topically treating skin eruptions such as warts and keratoacanthomas utilizing a topically effective amount of tazarotene in a suitable pharmaceutical composition. The composition contains about 0.01 to 2.0% by weight of tazarotene, preferably about 0.1%. Other types of skin eruptions include actinic keratoses, male genital warts, Bowenoid papulosis, and the like.

The composition can also contain 0.01 to 2.0% by weight of fluoroucil and/or a corticosteroid.

Among the topical corticosteroids which may be used in the present invention are triamcinolone acetonide, flurandrenolide, prednisone, amcinonide, dexamethasone, betamethasons valerate, halocinomide, clocortolone, hydrocortisone valerate and the like.

In accordance with the invention, the treatment of warts and keratoacanthoma involves a daily topical application of the compositions of the invention. The length of time of treatment depends on the severity of the disease. A mild case normally requires treatment of about 2 to 3 weeks.

The compositions of the invention may be used for the treatment of warts or keratoacanthomas in the form of aqueous, aqueous-alcoholic solutions, or in the form of creams, gels emulsions or foams or alternatively in the form of aerosol compositions also containing a propellent agent under pressure.

The amounts of the different constituents of the compositions according to the invention are those traditionally used in the pharmaceutical field.

When the composition of the invention is an emulsion, the proportion of the fatty phase can range from 5% to 80% by weight, and preferably from 5% to 50% by weight, relative to the total weight of the composition. The oils, emulsifiers and coemulsifiers used in the composition in emulsion form are chosen from those traditionally used in the pharmaceutical field. The emulsifier and the coemulsifier are present in the composition in a proportion ranging from 0.3% to 30% by weight, and preferably 0.5 to 30% or, better still, from 0.5 to 20%, by weight relative to the total weight of the composition. The emulsion can, in addition, contain lipid vesicles.

When the compositions of the invention is an oily gel or solution, the fatty phase can represent more than 90% of the total weight of the composition.

In a known manner, the composition of the invention may also contain adjuvants which are customary in the pharmaceutical field, such as hydrophilic or lipophilic gelling agents, hydrophilic or lipophilic active agents, preservatives, antioxidants, solvents and fillers. The amounts of these different adjuvants are those traditionally used in the pharmaceutical or dermatological field, and are, for example, from 0.01% to 10% of the total weight of the composition. Those adjuvants, depending on their nature, may be introduced into the fatty phase, into the aqueous phase and/or into lipid spherules.

As oils which can be used in the invention, mineral oils (liquid paraffin), vegetable oils (liquid fraction of shea butter, sunflower oil), animal oils (perhydrosquatene), synthetic oils (Purcellin oil), silicone oils (cyclomethicone) and fluorinated oils (perfluoro polyethers) may be mentioned.

As emulsifiers which can be used in the invention, glycerol stearate, polysorbate 60 and the PEG-6/PEG-32/glycol stearate mixture sold under the name Tefose® 63 by the company Gattefosse may be mentioned as examples.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allanloin, sugars and sugar derivatives, water-soluble vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features to the lesions when utilized, which promotes their removal.

The compositions of the invention may include plant or herbal extracts. For example, there may be utilized extracts of Paraguay tea, Kola and Guarana, which provide a source of methylxanthines, saponius, tannins and glycosides that have been shown to be anti-inflammatory and can be used to treat or prevent irritations from the active ingredients. The extract of Paraguay tea is known as "Mate extract" and is described in the "International Cosmetic Ingredient Dictionary", 5th Edition. Mate extract is commercially available in combination with extracts of Kola and Guarana which is sold by Cosmetic Ingredient Resources of Stamford, CT under the trademark "QUENCHT".

Each of mate extract and aloe vera extract are known to provide anti-inflammatory activity.

A surfactant can be included in the composition so as to provide deeper penetration of the ingredients. Many surfactants also possess anti-microbial activity.

The surfactants which can be used in the present compositions are the water soluble anionic, nonionic, amphoteric, zwitterionic or cationic surfactants. Most preferred is nonoxynol-9, which is an antiviral agent.

The following examples further illustrate the practice of this invention, but are not intended to be limiting thereof. It will be appreciated that the selection of actual amounts of drugs to be administered to any individual patient will fall within the discretion of the attending physician and will be prescribed in a manner commensurate with the appropriate dosages will depend on the stage of the disease and like factors uniquely within the purview of the attending physician.

EXAMPLE 1

A gel is prepared by admixing the following ingredients:

| Ingredient | Wt % |
| --- | --- |
| Carbomer 940 | 2.10 |
| Xantham gum | 0.15 |
| Propylene glycol | 51.94 |
| Dipropylene glycol | 15.00 |
| Ethoxydiglycol | 15.00 |
| Dimethylisosorbide | 11.00 |
| Aloe Vera gel | 2.00 |
| Surfactant | 0.05 |
| Dexamethasone | 2.00 |
| Tazarotene | 0.76 |
| | 100.00% |

EXAMPLE 2

A lotion is prepared by admixing the following ingredients:

| Ingredient | Wt % |
| --- | --- |
| Tazarotene | 1.10 |
| Propylene Glycol Stearate | 9.50 |
| Isocetyl alcohol | 8.00 |
| PEG-100 Stearate | 1.20 |
| Water | 69.90 |
| Hydrocortisone | 1.00 |
| Methyl paraben | 0.20 |
| Propylene glycol | 9.00 |
| Sorbitan palimate | 0.60 |
| Mate extract | 0.50 |
| | 100.00% |

EXAMPLE 3

A topical cream was prepared as follows:

| A. The following mixture was prepared: | |
| --- | --- |
| Triamcinolene acetonide | 2.0 g |
| Tarzarotene | 1.0 g |
| Olive oil | 5.0 g |
| Cetanol | 2.0 g |
| Stearic acid | 5.0 g |
| Glycerin aliphatic acid ester | 12.0 g |
| Tween 60 | 0.5 g |
| B. The following mixture was also prepared: | |
| Prophylene glycol | 0.5 g |
| Methyl paraben | 0.1 g |
| Propyl paraben | 0.02 g |
| Purified water to | 100 g in total |

The mixture of parts A and B were blended together by conventional means to give a total of 100 g. of 100% by weight topical cream which could be utilized for treatment of warts.

EXAMPLE 4

An oleaginous anhydrous ointment was prepared with the following composition:

| Composition | % |
| --- | --- |
| Dexamethasone | 2.0 |
| Tarzarotene | 2.0 |
| Soy phosphatide | 5.0 |
| Plastibase 50W | 90.95 |
| Butylated hydroxytoluene | 0.025 |
| Vitamin E | 0.025 |
| | 100.000 |

What is claimed is:

1. A method for topically treating non-metastasizing skin eruptions of warts on a patient which comprises applying an effective amount of a compound consisting of ethyl 6-[2-(4,4-dimethylthiochroman-6-yl]-ethynyl] nicotinate or the salts thereof as a sole active ingredient, in a suitable pharmaceutical composition to the site of the skin eruption.

2. The method of claim 1 wherein said compound comprises about 0.1 to 2.0% by weight of said composition.

3. The method of claim 1 including an effective amount of a corticosteroid.

4. The method of claim 1 including an effective amount of fluorouracil.

5. The method of claim 1 wherein said composition includes an anti-irritant.

6. The method of claim 5 wherein said anti-irritant is mate extract.

7. The method of claim 1 wherein said pharmaceutical composition is a gel.

8. The method of claim 1 wherein said composition is a lotion or creme.

9. The method of claim 1 including a surfactant.

10. The method of claim 9 wherein said surfactant is nonoxynol-9.

* * * * *